(12) United States Patent
Savage et al.

(10) Patent No.: US 6,437,179 B1
(45) Date of Patent: Aug. 20, 2002

(54) PROCESS FOR THE PREPARATION OF FLUOROGENIC PHENOLIC COMPOUNDS

(75) Inventors: M. Dean Savage; Edward K. Fujimoto, both of Rockford, IL (US)

(73) Assignee: Pierce Chemical Company, Rockford, IL (US)

( * ) Notice: Subject to any disclaimer, the term of this patent is extended or adjusted under 35 U.S.C. 154(b) by 0 days.

(21) Appl. No.: 09/642,515

(22) Filed: Aug. 18, 2000

Related U.S. Application Data

(63) Continuation of application No. 09/207,235, filed on Dec. 8, 1998, now abandoned.

(51) Int. Cl.[7] .................................................. C07C 65/03
(52) U.S. Cl. ........................ 562/478; 562/494; 568/753
(58) Field of Search ............................... 562/478, 494; 568/753; 252/182.31, 182.12, 18.29

(56) References Cited

FOREIGN PATENT DOCUMENTS

JP      4-234998     *  8/1992

* cited by examiner

Primary Examiner—Rosalynd Keys

(57) ABSTRACT

A method is disclosed for preparing a fluorogenic phenolic compound with improved optical qualities for use in formulating a substrate solution for assay of peroxidase or peroxide activity. The method involves forming a solution under anoxic conditions which contains the phenolic compound and an aminopolycarboxylic acid or aminopolyphosphonic acid, or salt thereof, metal chelating agent and, while the solution is maintained under anoxic conditions, recovering the compound from the solution in an optically enhanced condition. A composition of matter is also disclosed which includes the fluorogenic phenolic compound in crystal form and a trace quantity of the metal chelating agent.

4 Claims, 1 Drawing Sheet

PROCESS FOR THE PREPARATION OF FLUOROGENIC PHENOLIC COMPOUNDS

RELATED APPLICATION

This application is a continuation of application S.N. 09/207,235, filed on Dec. 8, 1998, which is now abandoned.

CROSS REFERENCE TO RELATED APPLICATIONS

This application is a continuation of U.S. application Ser. No. 09/207,235 filed Dec. 8, 1998, now abandoned.

FIELD OF THE INVENTION

The present invention relates to fluorometric assays and, more particularly, to improved fluorogenic compounds for use in assays for the determination of peroxidase or peroxide.

BACKGROUND OF THE INVENTION

Zaitsu and Ohkura, Analytical Biochemistry, 109, 109–113 (1980) describe the use of Phenolic compounds as fluorogenic substrates for the horseradish-peroxidase (HRP)-mediated reaction with hydrogen peroxide in order to assay for peroxidase activity or the peroxide. Of the fluorogenic substrates, 3-(p-hydroxyphenyl)propionic acid (HPPA) was identified as being preferred in providing a rapid and sensitive assay. Tuuminen, et al., Journal of Immunoassay, 12(1), 29–46 (1991) recognized the observations of Zaitsu and Ohkura and applied the use of HPPA as a fluorogenic substrate of labelled HRP in an immunoassay.

A limitation accompanying the use of HPPA as a fluorogenic substrate for peroxidases used as labelling enzymes in enzyme immunoassay methods was recognized in Japanese Patent Application No. 4-234998 filed on Dec. 27, 1990, by Kohusai Shiyaku K. K. It was observed that peroxidase-mediated enzyme immunoassay methods using HPPA were intrinsically highly sensitive, but that HPPA formulated in buffers to provide the substrate solution undergoes condensation as a result of the presence of metal ions and is converted into a fluorescent substance which results in a rise in the reagent blank, thus decreasing sensitivity and measurement precision. The Japanese patent application discloses that a chelating agent such as an aminopolycarboxylic acid or aminopolyphosphonic acid, or salts thereof, can be used to stabilize formulated HPPA substrate solutions by reducing the rise in the reagent blank.

While demonstrating an improvement in the assay following the technique illustrated in the Japanese application and other cited literature, there is still room for improvement in the assay. With commercially available fluorogenic phenolic material, or such material purified by conventional techniques, for use as a primary material in formulating a fluorogenic peroxidase substrate, heretofor unrecognized limitations are imposed with respect to the substrate's utility. One limitation results because of the presence of superoxidation product(s) (as distinguished from oxidative formation of the fluorescent product of HPPA) in the primary material. The superoxidation product(s) have now been discovered as being detrimental because they possess interfering optical qualities which decrease the fluorescent response via an absorptive mechanism (i.e. a filtering effect) within the excitation/emission spectrum of the fluorescent product. This decreases the sensitivity of the substrate when used subsequently in assays. Purification of commercially available material by conventional recrystallization techniques does not result in reduction in the above mentioned superoxidation products.

Additionally, it is has not been heretofore recognized that the background fluorescence of the starting material can be influenced by the manner in which the material is purified; it being assumed that background fluorescence is strictly an intrinsic property of the starting material Accordingly, conventional methods of purification of starting material have not addressed the removal of oxidative products in the starting material which give rise to background fluorescence. Accordingly, low signal to noise ratios accompany the use of such starting materials. And, consequently, both primary materials (before or after conventional purification) that are generally accepted for preparing substrate solutions result in non-optimum assays with respect to high background (decreased signal to noise ratio) and/or decreased sensitivity.

SUMMARY OF THE INVENTION

Now in accordance with the present invention, there is provided means for preparing improved fluorogenic phenolic compounds for use as primary materials in preparing substrates with fluorogenic activity in peroxide-mediated assays of peroxidase activity or peroxidase-mediated assays of peroxide. The method provides the phenolic compound in an optically enhanced condition by controlling the presence of superoxidation products while concurrently yielding primary material for use in formulating substrate solutions which have low background fluorescence. The method involves forming under anoxic conditions, i.e. decreased oxygen concentration, a solution which contains a fluorogenic phenolic compound and an aminopolycarboxylic acid or aminopolyphosphonic acid, or salt, thereof, metal chelating agent and, while the solution is maintained under anoxic conditions, recovering the compound from the solution, by for example, crystallization. As so recovered, the compound is in an optically enhanced condition.

The method disclosed herein is contrary to conventional wisdom which teaches against the addition of extraneous substances in crystallization procedures. The method disclosed herein is also contrary to conventional wisdom which instructs the use of activated carbon for removal of optical impurities; the use of which is detrimental to phenolic compounds prepared for use as primary materials for subsequent use in formulating fluorogenic peroxidase substrates.

In further keeping with the present invention another aspect thereof provides a composition of matter with improved optical performance characteristics for use in formulating a fluorogenic substrate solution in peroxide-mediated assays of peroxidase activity or peroxidase-mediated assays of peroxide. The composition contains a fluorogenic phenolic compound in crystal form and a trace quantity of an aminopolycarboxylic acid or aminopolyphosphonic acid, or salt thereof, metal chelating agent, which copurifies with the fluorogenic phenolic compound and which can also arise from the admixture of the metal chelating agent with the compound during washing procedures. Typically, such agents would be present in amount of less than 0.3% by weight, but higher concentrations are not necessarily detrimental since the chelating agent is generally included in the substrate solution from which the phenolic compound is prepared.

The composition of matter above described can be further characterized as having an optical quotient of less than about 1.1 and preferably about 1.0. As used herein, the optical quotient is defined as the ratio of the relative fluorescence (RFU) of a 5 mg/ml concentration of the compound, dissolved in 0.3 M glycine, 2 mM EDTA, pH 10.5 buffer, as compared to the relative fluorescence of a 10 mg/ml concentration of the compound when dissolved in the same buffer, both fluorescent measurements being made after approximately the same elapsed time once the fluorescence intensities of the two solutions have stabilized and under the substantially the same conditions. Having an optical quotient, as above identified, defines the absence of products detrimental to the optical qualities of the fluorogenic phenolic primary material. The detrimental products provide a filtering effect which results in a decrease in fluorescence as concentration increases, and a corresponding increase in optical quotient.

The above described fluorogenic material has reduced intrinsic background fluorescence which is otherwise associated with material not prepared in accordance with the present invention. In this respect, background fluorescence of the fluorogenic phenolic material of the present invention is reduced by at least 3% as compared with the background fluorescence of the parent material from which it is purified, even where the parent material is considered to be highly qualified for use as a primary material.

DESCRIPTION OF THE INVENTION

Figure 1:
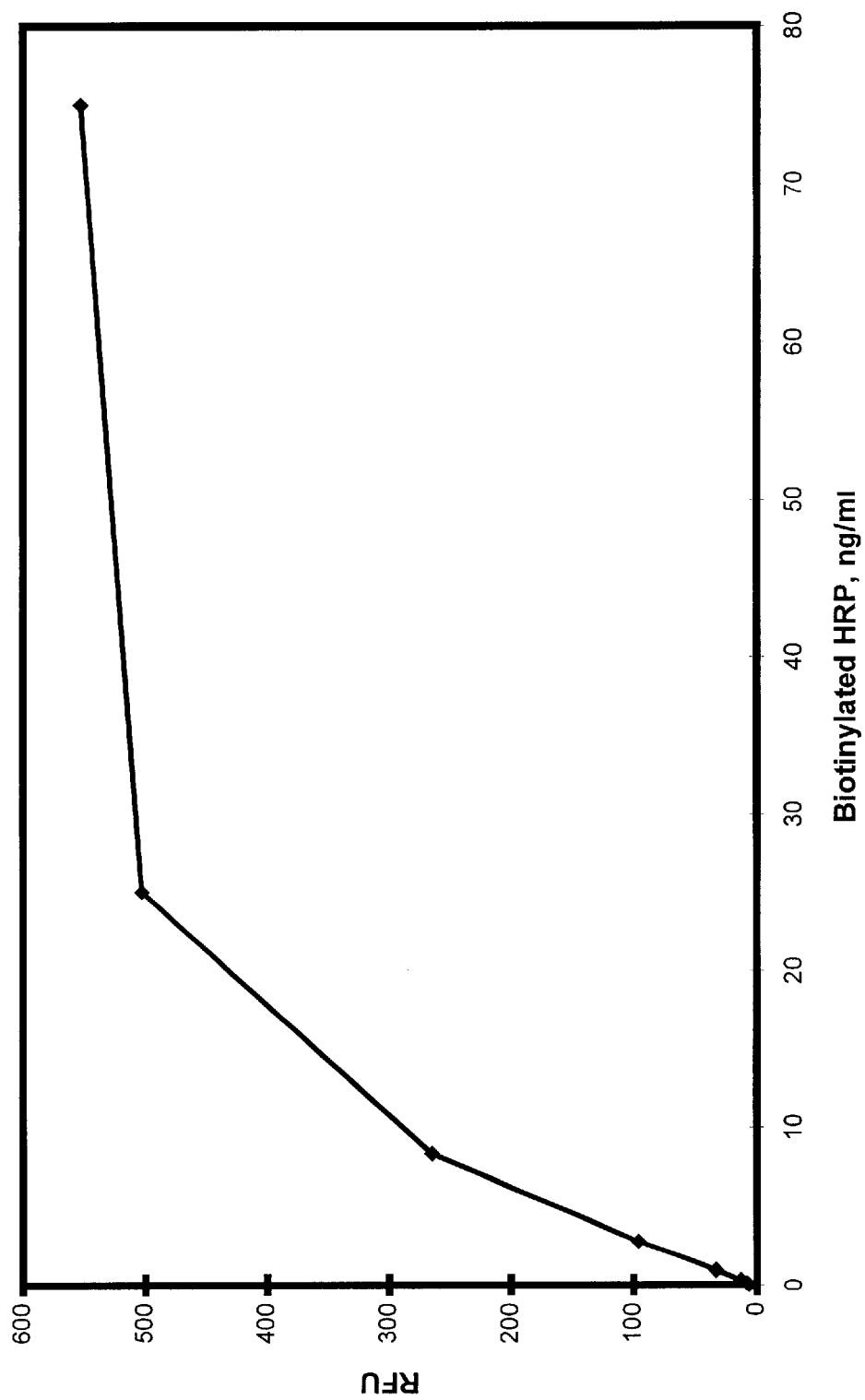
FIG. 1 illustrates a standard curve for a peroxidase assay using HPPA primary material prepared in accordance with the present invention.

The method described herein is applicable for improving optical performance characteristics of a large number of phenolic fluorogenic compounds for peroxidase/peroxide assays. These compounds have been identified in the literature such as in the above identified Zaitsu and Ohkura publication. Particularly useful are those p-hydroxyphenyl compounds identified therein with a substituent having 2 or 3 methylene groups, without a 3-methoxy group. 3-(4-hydroxyphenyl)propionic acid (HPPA) and p-tyrosol are identified as particularly preferred with horseradish peroxidase as the enzyme.

An important aspect of the present invention is that the starting fluorogenic phenolic compound be purified from solution under anoxic conditions and in the presence of an aminopolycarboxylic acid or aminopolyphosphonic acid, or salts thereof, metal chelating agents. Anoxic solutions are conveniently prepared via sparging of solutions with an inert gas, such as nitrogen or argon and the anoxic conditions are further maintained by providing an inert gas blanket.

Concerning the metal chelating agents, preferably, these chelating agents contain three or more alkylene carboxylic acid groups or alkylene phosphonic acid groups bonded to nitrogen. While ethylenediaminetetraacetic acid (EDTA), particularly in the form of its disodium salt, is preferred, other particularly useful chelating agents of this type are the following identified acids, as well as their salts: diethylenetriaminepentaacetic acid, diaminopropanoltetraacetic acid, triethylenetetraminehexaacetic acid, glycol ether diaminetetraacetic acid, nitrilotriacetic acid, ethylenediaminetetrakis (methylenephosphonic acid), ethylenediaminediacetic acid, ethylenediaminepropionic acid, hydroxyethylethylenediaminetriacetic acid, iminodiacetic acid. In forming the solution, the concentration of the metal chelating agent should in the concentration range of 0.001 mM to 100 mM and preferably be in the concentration range of 0.1–5 mM.

In accomplishing recovery of the fluorogenic phenolic compound from solution, crystallization is preferred. However, other recovery techniques accomplished under anoxic conditions with metal chelators, such as high performance or conventional liquid chromatography, can be used. In practice, with care taken to maintain anoxic conditions throughout the procedure, an aqueous supersaturated solution at elevated temperature of the phenolic compound and the metal chelating agent is first prepared followed by filtration and subsequent cooling to ambient temperature to crystallize the compound from solution. The crystallized compound is then filtered away from the mother liquor and then further washed with anoxic water containing the metal chelating agent, followed by drying under nitrogen. The resulting compound while containing trace quantities of the metal chelating agent, can be used as a primary material for fluorogenic peroxidase substrate solutions with no additional treatment, and the resulting compound is stable in its crystal form under aerobic conditions.

The method described herein is useful for the preparation of fluorogenic phenolic compounds with consistently improved optical performance characteristics for use in fluorometric peroxide-mediated assays of peroxidase activity or fluorometric peroxidase-mediated assays of peroxide. When this method is practiced under large-scale conditions (i.e. greater than 25 g scale), the obtained benefits are particularly enhanced as compared to the use of either commercially available material or conventionally purified material. Formulations of fluorogenic phenolic-based substrate solutions and accompanying methods for using such solutions in accomplishing the above mentioned assays are well known and have been described previously in the literature, such as those cited above. Substrate solutions formulated according to the before identified Japanese application which contains metal chelators for stabilization of the prepared substrate are considered to be particularly useful when using a fluorogenic phenolic compound of the present invention.

The fluorogenic phenolic compounds of the present invention having the improved optical performance characteristics described herein also exhibit lower intrinsic fluorescence as purified; it being recognized that lower intrinsic fluorescence correlates with lower background when the primary material is subsequently used to formulate a fluorogenic substrate solution. Lower background, in turn, allows for higher attainable signal to noise ratios. Accordingly, the background fluoresence of optically enhanced fluorogenic phenolic primary material of the present invention is reduced by at least 3% as compared to the background fluorescence of the parent material from which it purified, even where the parent material is considered to be highly qualified for use as a primary material.

EXAMPLE I

Into a four liter reaction flask equipped with a magnetic stirrer and thermometer was placed 360.04 g HPPA (greyish color, melting point of 128–130 degrees C.) obtained from Aldrich Chemical Co. (Catalog No. H5240–6) followed by addition of 2.88 liters of anoxic EDTA/water solution (prepared by dissolving 1.49 g disodium EDTA in 4 liters of MilliQ water followed by nitrogen sparging, 1 mM final concentration with respect to EDTA). The solution was heated to 68 degrees Celsius and then filtered into a clean 4 liter suction flask over a glass filter pad to yield a clear solution with a strong yellow cast. The solution was allowed to stand overnight under a nitrogen atmosphere prior to initialization of crystallization with HPPA seed material which then progressed for approximately 4 hours. The solution was then slurried mechanically using a Hershberg stirrer for 2.5 hours followed by filtration over a Whatman # 1 filter paper using an additional 2 liters of anoxic EDTA/water solution for washing the crystals. The crystals were partially dried for 30 minutes using a nitrogen sweep, and then transferred to a dish where the damp needle crystals were further dried under vacuum over sodium hydroxide for several days. The resultant material weighed 254.6 g for a yield of 70.7% and the crystals were whitish in color with a melting point of 125–126 degrees C., the decreased melting point range of the purified material being indicative of the removal of the trace quantities of the heterogeneous super-oxidation products. Based on the yield of HPPA, EDTA was considered to be present in an amount of less than about 0.3% (~0.75 g) by weight.

A 0.3 M glycine, 2 mM EDTA, pH 10.5 aqueous buffer was prepared. The material purified as described above was dissolved in this buffer at the following two concentrations: 5 mg/ml and 10 mg/ml. In like fashion, the starting Aldrich material was also dissolved separately in the same buffer at the same concentrations. The four solutions were measured periodically for relative fluorescence at 320/430 excitation/emission until equilibrium was reached. A BMG PolarStar microplate reader in prompt fluorescence mode was used for instrumentation, with 200 μl per well of each of the aforementioned solutions deposited in an opaque white CoStar microplate. Table I sets forth the relative fluorescence of the four solutions, after correcting for the buffer blank, along with the derived optical quotients, after 4 hours.

TABLE I

|  | Example I Material | | Starting Material | |
| --- | --- | --- | --- | --- |
|  | 5 mg/ml | 10 mg/ml | 5 mg/ml | 10 mg/ml |
| RFU | 5860 | 5814 | 5585 | 4705 |
| Optical Quotient | 1.01 | | 1.19 | |

Additionally, the 5 mg/ml concentration RFU values given in the table illustrate that the intrinsic background fluorescence of the Example I material is approximately 3% lower as compared with the starting material, which would have ordinarily been considered to be high quality primary material.

The following example illustrates the use of primary material prepared according to Example I in connection with the assay of peroxidase activity.

EXAMPLE II

Biotinylated HRP diluted in PBS buffer (0.1 M sodium phosphate, 150 mM NaCl, pH 7.4) was bound at 100 μl per well to a Neutravidin coated white microplate (96-well) at varying concentrations of 0–75 ng/ml, the 75 ng/ml concentration being selected to exceed the maximum for binding of biotinylated HRP onto the coated plate surface, for 1 hour at room temperature with mild shaking followed by 3×200 μl washes with PBS.

To the prepared microplate, 100 μl of HPPA working solution was added to each well. This working solution was prepared by adding 58 μl of 120 mM sodium perborate, 0.1 M sodium acetate, pH 5.0 to 1.74 ml of 22 mM HPPA, 2 mM disodium EDTA, 0.1 M Tris, pH 8.1, with final adjustment to 2 ml volume with MilliQ water. Reaction with HRP proceeded for 50 minutes at room temperature after which time the plate was read on a Perkin-Elmer LS50 fluorometer using 320/420 nm excitation/emission wavelengths with 10/4.2 nm slit widths and PMT voltage set to 900 mV. The results of the fluorometric readings are illustrated in FIG. 1.

What is claimed is:

1. A method for preparing a fluorogenic phenolic compound with improved optical qualities for use in formulating a substrate solution for assay of peroxidase or peroxide activity comprising forming under anoxic conditions a solution which contains said compound and an aminopolycarboxylic acid or aminopolyphosphonic acid, or salt thereof, metal chelating agent and, while said solution is maintained under anoxic conditions, recovering said compound from the solution in an optically enhanced condition.

2. The method of claim 1 wherein the compound is recovered from solution by crystallizing the compound out of the solution.

3. The method of claim 2 wherein the metal chelating agent is ethylenediaminetetraacetic acid or the salt thereof.

4. The method of claim 2 wherein the fluorogenic phenolic compound is 3-(p-hydroxyphenyl)propionic acid.

* * * * *